(12) United States Patent
Point et al.

(10) Patent No.: US 11,035,759 B2
(45) Date of Patent: Jun. 15, 2021

(54) DEVICE FOR DETECTING AT LEAST ONE CHEMICAL SPECIES, INCLUDING A CHEMICAL SENSOR, AND METHOD FOR MANUFACTURING SUCH A CHEMICAL SENSOR

(71) Applicant: INSTITUT DE RECHERCHE POUR LE DEVELOPPEMENT (IRD), Marseilles (FR)

(72) Inventors: David Point, Lanton (FR); Anthony Gautier, Notre Dame d'oe (FR)

(73) Assignee: INSTITUT DE RECHERCHE POUR LE DEVELOPPMENT (IRD), Marseilles (FR)

( * ) Notice: Subject to any disclaimer, the term of this patent is extended or adjusted under 35 U.S.C. 154(b) by 394 days.

(21) Appl. No.: 15/549,675

(22) PCT Filed: Feb. 11, 2016

(86) PCT No.: PCT/FR2016/050317
§ 371 (c)(1),
(2) Date: Aug. 9, 2017

(87) PCT Pub. No.: WO2016/128686
PCT Pub. Date: Aug. 18, 2016

(65) Prior Publication Data
US 2018/0017468 A1 Jan. 18, 2018

(30) Foreign Application Priority Data
Feb. 13, 2015 (FR) ..................................... 15 51224

(51) Int. Cl.
*G01N 1/10* (2006.01)
*G01N 33/18* (2006.01)
(Continued)

(52) U.S. Cl.
CPC ............... *G01N 1/10* (2013.01); *B05D 1/005* (2013.01); *B05D 1/18* (2013.01); *G01N 33/1813* (2013.01)

(58) Field of Classification Search
CPC ........ G01N 1/10; G01N 33/1813; B05D 1/18; B05D 1/005
See application file for complete search history.

(56) References Cited

U.S. PATENT DOCUMENTS 7,135,295 B1 * 11/2006 Willner .................. C07K 16/00
435/7.1
7,473,551 B2 * 1/2009 Warthoe ............... G01N 29/226
435/287.2
(Continued)

FOREIGN PATENT DOCUMENTS

| EP | 0 713 576 A1 | 5/1996 |
|----|--------------|--------|
| EP | 2 484 630 A1 | 5/1996 |
| WO | 95/05591 A1 | 2/1995 |

OTHER PUBLICATIONS

Casilli S et al.: "Piezoelectric sensor functionalised by a self-assembled bipyridinium derivative: characterisation and preliminary applications in the detection of heavy metal ions", Biosensors and Bioelectronics, Elsevier BV, NL, vol. 20, No. 6, Dec. 15, 2004 (Dec. 15, 2004), pp. 1190-1195, XP004648763, ISSN: 0956-5663, DOI: 10.1016/J.BIOS.2004.04.028.
(Continued)

*Primary Examiner* — Lore R Jarrett
(74) *Attorney, Agent, or Firm* — Nixon & Vanderhye

(57) ABSTRACT

Disclosed is a device for detecting at least one chemical species in a medium to be analyzed including a chemical sensor, the chemical sensor including: a substrate; a functionalized carrier intended for capturing and accumulating the chemical species and attached to a side of the substrate. The device also includes a unit for diffusion between the
(Continued)

medium to be analysed and the functionalised carrier. The diffusion unit includes a vibration generating system connected to the chemical sensor in order to subject the chemical sensor to controlled vibrations.

11 Claims, 5 Drawing Sheets

(51) Int. Cl.
*B05D 1/00* (2006.01)
*B05D 1/18* (2006.01)

(56) References Cited

U.S. PATENT DOCUMENTS

2006/0133953 A1* 6/2006 Zhang .................. B82Y 15/00
422/400
2014/0076024 A1* 3/2014 Duraffourg ............ G01N 25/18
73/23.4

OTHER PUBLICATIONS

Denise P Ruys et al.: "Mercury detection in air using a coated piezoelectric sensor", Analytica Chimica Acta, vol. 404, No. 1, Jan. 1, 2000 (Jan. 1, 2000), NL, pp. 95-100, XP055227851, ISSN: 0003-2670, DOI: 10.1016/S0003-2670(99)00673-X.
Rodriguez Gutierrez J A et al.: "Development of ionoselective electrochemical sensors by using the sol-gel process", Analytica Chimica Acta, Elsevier, Amsterdam, NL, vol. 524, No. 1-2, Oct. 25, 2004 (Oct. 25, 2004), pp. 339-346, XP004582530, ISSN: 0003-2670, DOI: 10.1016/J.ACA.2004.02.066.
Sabri Y M et al.: "Mercury diffusion in gold and silver thin film electrodes on quartz crystal microbalance sensors", Sensors and Actuators B: Chemical: International Journal Devoted to Research and Development of Physical and Chemical Transducers, Elsevier S.A, CH, vol. 137, No. 1, Mar. 28, 2009 (Mar. 28, 2009), pp. 246-252, XP025962274, ISSN: 0925-4005, [retrieved on Dec. 3, 2008], DOI: 10.1016/J.SNB.2008.11.032.
International Search Report, dated May 23, 2016, from corresponding PCT/FR2016/050317 application.

* cited by examiner

DEVICE FOR DETECTING AT LEAST ONE CHEMICAL SPECIES, INCLUDING A CHEMICAL SENSOR, AND METHOD FOR MANUFACTURING SUCH A CHEMICAL SENSOR

BACKGROUND OF THE INVENTION

Field of the Invention

The invention relates to the field of measuring the concentration of chemical species in a fluid, and more particularly to the field of measuring the concentration of inorganic, molecular or biological species in a body of water.

Description of the Related Art

Human activities require the pollutants in ecosystems to be monitored for reasons concerning both health and environmental impact studies. These pollutants can be produced naturally in ecosystems (e.g. biotoxins) or be themselves a result of human activities. Among the pollutants the most problematic in this regard are trace metals, and more particularly mercury. One specific application of the invention therefore lies in the detection of toxic forms of mercury, however is not restricted thereto.

Natural sources of mercury are relatively numerous. For the purpose of illustration, examples such as volcanic emissions can be cited, which release mercury, in addition to passive emissions to the atmosphere from oceans or inland waters. Human activities involving the use of fossil fuel also release mercury into the atmosphere. Therefore, substantial quantities of mercury can be found in the environment.

However, the physical and chemical attributes and toxicity levels of mercury depend on the different chemical forms thereof. In particular, mercury in the air falling into water (rivers, lakes, seas, oceans, etc.) can be converted into an organometallic compound, such as methylmercury (written as MeHg), which is the most toxic form of mercury's organometallic compounds. The toxic nature of MeHg has driven the health authorities in many countries to define concentration thresholds that must not be exceeded in foods such as fish.

The mechanisms behind the formation of MeHg, by a process called mercury methylation, are relatively unknown. Indeed, in aquatic environments, mercury can be found in different forms, comprising dissolved elemental mercury and inorganic mercury which, in each of said forms, are capable of being transformed into MeHg. It is estimated that about 1 to 30% of the total mercury, depending on the ecosystems, is suitable for undergoing the methylation process. Conversely, MeHg can undergo demethylation. Therefore, the simple actual measurement of the total mercury concentration does not provide information on mercury toxicity.

It is therefore necessary to take into account all health and environmental risks as a result of the mercury, to measure these different chemical forms, the bioavailability thereof, the complexes formed thereof with counter-ions or the organic matter, and the stability thereof.

The process of determining the concentration of species to be analysed is known and based on Fick's laws, governing the diffusion phenomenon between the ambient medium and a preconcentration substrate. In particular, depending on the diffusion time, i.e. the time during which the species are captured on an appropriate substrate, and with knowledge of the diffusion coefficient, the quantity of species captured can be linked to the concentration thereof.

The detection of species by diffusion, in order to apply the Fick's laws, takes place for example using a passive sensor such as the DGT (Diffusive Gradient in Thin film) sensor.

The DGT sensor is used in general to measure the quantity of a species in a liquid medium, even when said species is present at a very low concentration.

The DGT sensor is present in the form of a preconcentration substrate intended to be immersed in a liquid. In the substrate, a layer of a first permeable gel, called a diffusive layer, is superposed with a preconcentration layer, which is constituted from a second gel comprising resin particles, called a resin layer. The diffusive layer comprises a surface portion uncovered by the substrate, in contact with the liquid. The size of the pores of the diffusive layer enable the maximum size of the species that will reach the resin layer to be determined. The species to be measured diffuse through the diffusive layer as far as the resin, where they become trapped by the resin particles and where they become concentrated. By having knowledge of the surface area of the sensor, the thickness of the diffusive layer, the diffusion coefficient of the species in the gel, the sensor immersion time and by measuring the concentration of the species accumulated in the resin layer, the concentration of species in the liquid medium to be analysed can be calculated. The longer the immersion time, the higher the concentration of trapped species. More specifically, after the DGT sensor has been immersed for a determined duration, it is retrieved. The resin particles are extracted from the resin layer and are analysed to obtained the concentration of trapped species.

Document EP 0 713 576 presents the DGT sensor. As explained herein, the thickness of the gel layers is not necessarily the only aspect that must be taken into account. Indeed, in practice, at the interface between the diffusive layer in contact with the liquid and the liquid, an intermediary diffusive layer is formed, called the Diffusive Boundary Layer (DBL). The DBL corresponds to the area in the liquid wherein any analyte trapped by the sensor is renewed by the external medium to compensate for the disappearance and thus restore the balance. The thickness of the DBL therefore contributes to the total diffusion pathway of the analytes.

In this document, it is explained that the DBL may or may not be disregarded, depending on the medium to be analysed. In order to disregard the DBL, the diffusive layer must have a minimum thickness such that it is far greater than that of the DBL. For example, whereas in an agitated medium, the thickness of the DBL is 0.1 mm at most, by giving the diffusive layer a thickness of 1 mm, the thickness of the DBL can be disregarded in the calculation of the ion concentration. However conversely, in a medium such as stagnant water, the DBL can reach 1 mm. Therefore, for this type of medium, this thickness must be taken into account in the calculation of the ion concentration.

Nonetheless, it is understood that the longer the diffusion pathway, formed by the thickness of the diffusive layer and that of the DBL, the longer the diffusion time, i.e. the time required for the species to pass through the DBL and the diffusive layer and become fixed in the resin layer. Therefore, by imposing a minimum thickness to the diffusive layer, a minimum sensor immersion time is also imposed in order to obtain a concentration in the resin layer that can be exploited. Moreover, the model for calculating the concentration in the medium to be analysed depends on the conditions in said medium. More specifically, when the current is weak, the thickness of the DBL must be taken into account. A question therefore arises concerning how said thickness is determined, with the resulting errors caused by the approximations.

There is thus a need for a new system for detecting a chemical substance that in particular overcomes the aforementioned drawbacks.

BRIEF SUMMARY OF THE INVENTION

Therefore, a first aspect of the invention involves proposing a system for detecting at least one chemical species allowing, after a period of immersion in the medium to be analysed that is shorter than in the prior art, an accumulation of said substance to be obtained, said accumulation being sufficient for the exploitation thereof for the calculations.

A second aspect of the invention involves proposing a system for detecting at least one chemical species allowing the thickness of the DBL to be controlled, regardless of the conditions of the medium to be analysed, and allowing the thickness thereof to be varied in order to modify the sensing dynamic of the sensor.

A third aspect of the invention involves being able to divide chemical species into size classes by adding a diffusive nanofilm layer between the ambient medium and a functionalised carrier.

A fourth aspect of the invention involves proposing a system for autonomously detecting at least one chemical species that can operate on any terrain in an in-situ manner.

A fifth aspect of the invention involves proposing a system for detecting at least one chemical species allowing results to be obtained with increased precision.

A sixth aspect of the invention involves proposing a system for detecting at least one species that is easy to handle.

To this end, a first purpose of the invention is to propose a device for detecting at least one chemical species in a medium to be analysed comprising a chemical sensor. The chemical sensor comprises:
  a substrate,
  a functionalised carrier intended for capturing and accumulating the chemical species and attached to a side of the substrate.

The device also comprises means for diffusion between the medium to be analysed and the functionalised carrier. The diffusion means comprise a vibration generating system connected to the chemical sensor in order to subject the chemical sensor to controlled vibrations.

The detection device is therefore the foundation of a diffusion phenomenon controlled by vibrations. However, the diffusion is required by the detection device as it is used to deduce the concentration of the chemical species targeted. By controlling the diffusion, a concentration measurement can be obtained with improved accuracy, and for a reduced measuring time relative to that of the prior art.

The device can comprise the following characteristics, which can be implemented alone or in any combination:
  the diffusion means comprise a diffusive layer superimposed on the functionalised carrier, the diffusive layer providing a selection of chemical species to be diffused;
  the diffusive layer is preferably less than 1 micrometre, or lies in the range 250 nm to 10 nm, such that the diffusion therethrough takes place more quickly than in the prior art;
  the diffusive layer is made from Agarose gel, particularly well suited to the detection of the chemical species of mercury;
  the thickness of the functionalised carrier is less than 1 micrometre or less than 1 nm;
  the substrate comprises two opposite sides, on each of which is adhered a functionalised carrier, so as to double the diffusion surface areas on the same substrate;
  the vibration generating system comprises a vibration sensor connected to the chemical sensor, which is used to control the vibrations effectively transmitted to the chemical sensor;
  the vibration generating system comprises a high-frequency vibrating micro-motor connected to the chemical sensor and to control means of the micro-motor;
  on the one hand, the device comprises a control unit in which the control means of the micro-motor are arranged, and on the other hand the device comprises a chemical head comprising the chemical sensor and the vibration generating system. The control unit and the chemical head can be removed from each other and each comprise at least one connection tip for the assembly thereof with each other. The chemical head can therefore be easily replaced after each measurement, while preserving the unit; and
  the detection device is present in the form of a single unit.

A second purpose of the invention is to propose a method for determining the concentration of at least one chemical species in a medium to be analysed by means of a detection device such as that disclosed hereinabove. The method comprises the steps of:
  placing the chemical sensor in contact with the medium to be analysed;
  subjecting the chemical sensor to vibrations at frequencies controlled by the vibration generating system;
  detecting the chemical species to be analysed by the functionalised carrier by diffusion between the medium to be analysed and the functionalised carrier;
  after a determined duration, retrieving the chemical sensor out of the medium to be analysed;
  extracting the chemical species trapped in the chemical sensor;
  by using the diffusion principle and the determined duration, determining the concentration of the chemical species to be analysed.

The frequency of the vibrations lies in the range 2 to 1,000 Hz, or in the range 10 to 600 Hz, in order to optimise the diffusion phenomenon. The vibrations can be adjusted to suit the agitation already present in the medium to be analysed.

According to one embodiment of the method, at least one chemical species is methylmercury, a species that is particularly toxic to humans.

A third aspect of the invention involves proposing a method for manufacturing a chemical sensor of a detection device as disclosed hereinabove, comprising the steps of:
  etching at least one side of a plate forming the substrate,
  adhering a functionalised carrier to the etched side of the substrate, the functionalised carrier having a thickness of less than 1 micrometre;
  depositing, by spin-coating or dip-coating, a diffusive layer onto the functionalised carrier, the diffusive layer having a thickness of less than 1 micrometre.

BRIEF DESCRIPTION OF THE DRAWINGS

Other advantages and applications will appear upon reading the description provided with reference to the accompanying figures, in which.

DETAILED DESCRIPTION OF THE PREFERRED EMBODIMENTS

Figure 1:
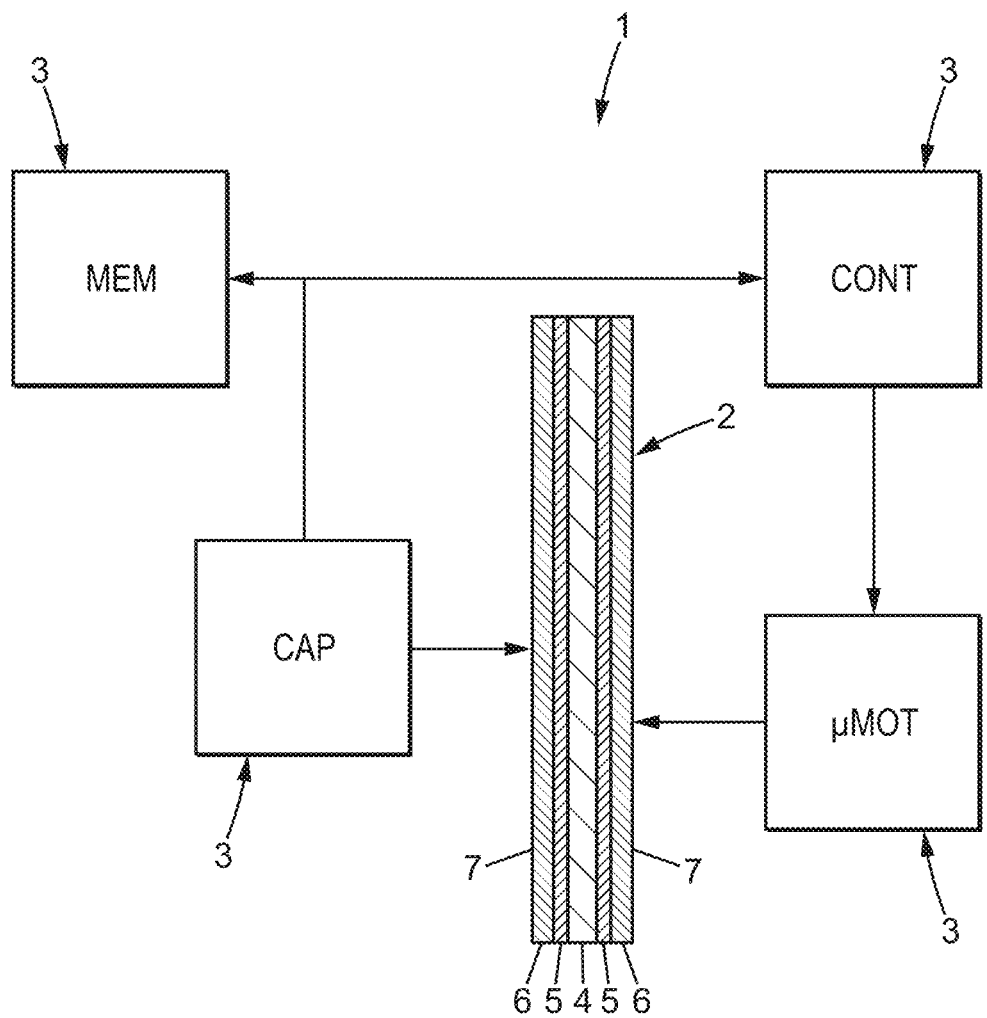
FIG. 1 is a diagrammatic view of one example embodiment of a device for detecting at least one chemical substance.

FIG. 1 shows a diagrammatic view of one example embodiment of a device 1 for detecting at least one chemical species. A chemical substance is understood hereinbelow as any type of species in the broadest sense thereof, in particular pollutants in a given environment, such as trace metals and the complexes thereof, molecules, but also biological species such as DNA fragments.

The detection device 1 comprises at least one chemical sensor 2, i.e. a sensor capable of trapping at least one chemical species. The chemical species to be captured will be considered hereinafter to be, in a non-limiting manner, a mercury compound, in particular MeHg. In practice however, the sensor 2 is intended to capture a plurality of species, such as a plurality of mercury compounds capable of undergoing methylation. The detection device 1 further comprises means for diffusion between the medium to be analysed and the chemical sensor 2. The diffusion means are defined as being any means through which a controlled diffusion phenomenon occurs. Indeed, as explained hereinbelow, the principle of the chemical sensor 2 is based on the diffusion phenomenon, enabling the determination of the concentration of the chemical species in the medium to be analysed. The use of the chemical sensor 2 therefore involves the implementation of a diffusion phenomenon in a controlled manner. For this purpose, the diffusion means comprise a vibration generating system 3 connected to the chemical sensor 2, so as to subject the chemical sensor 2 to controlled vibrations.

Figure 2:
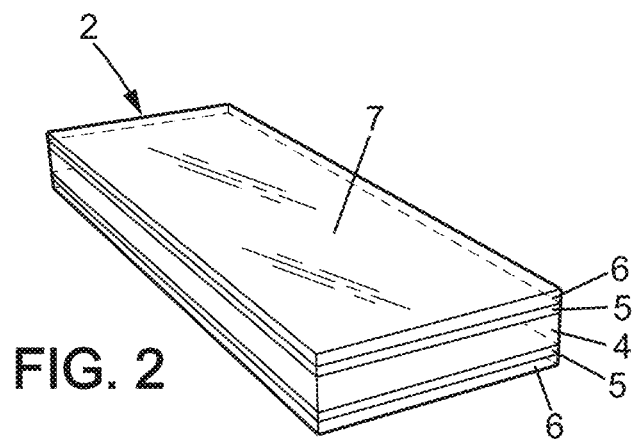
FIG. 2 is a diagrammatic view of a chemical sensor of the device in FIG. 1.
Figure 3:
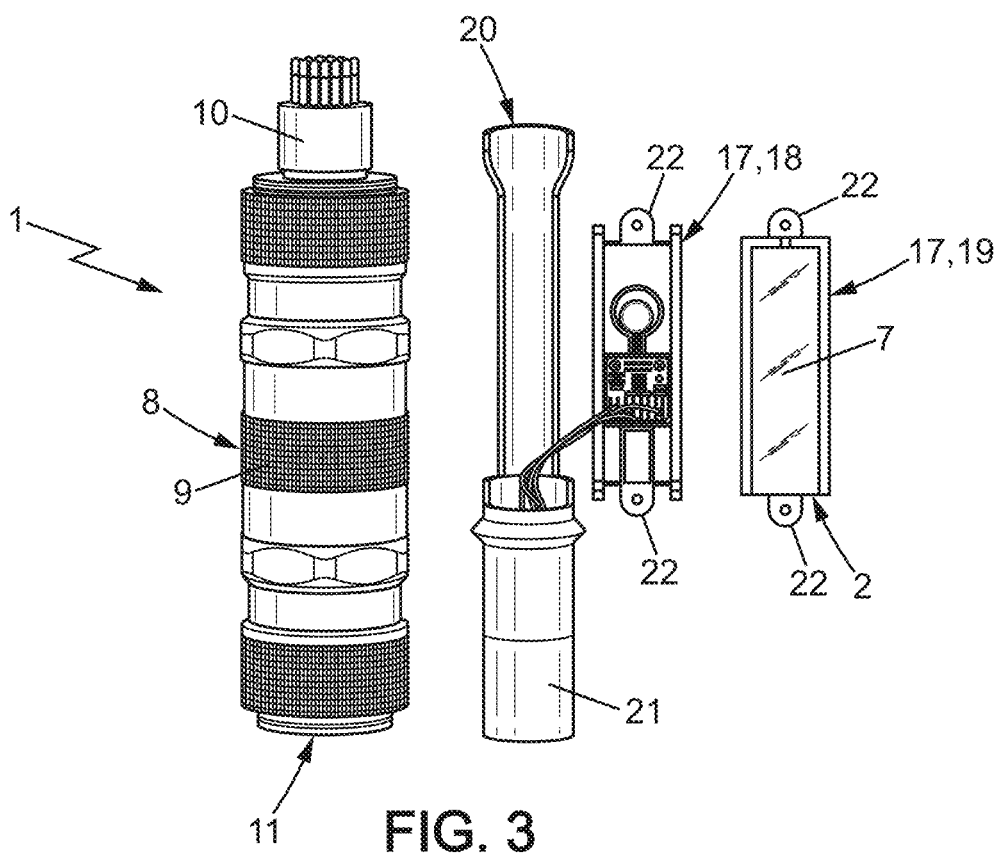
FIG. 3 is an exploded view of the detection device in FIG. 1 according to one embodiment.
Figure 4:
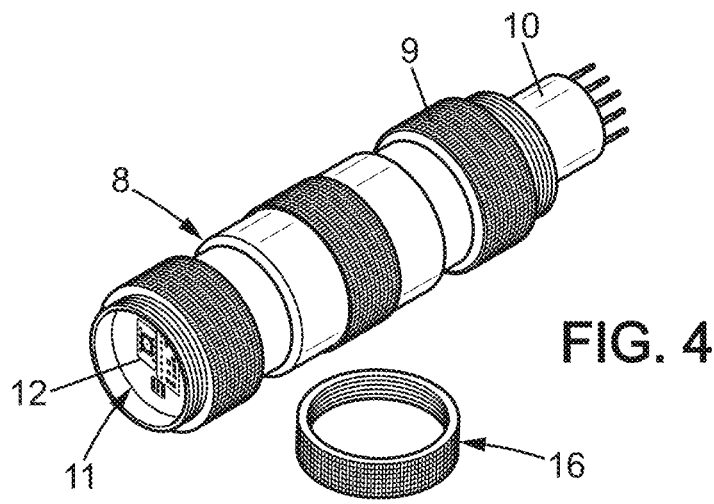
FIG. 4 is a view of a unit composing the detection device in FIG. 3.
Figure 5:
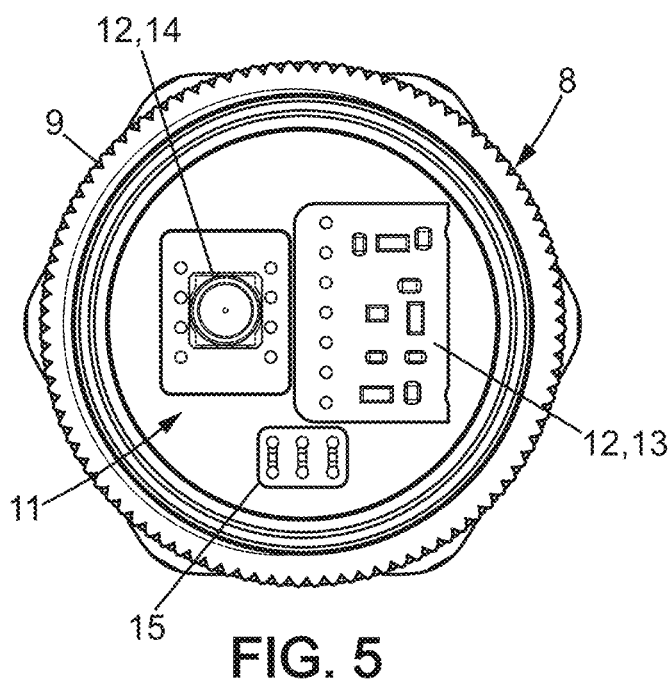
FIG. 5 is a view of one end of the unit in FIG. 4.
Figure 6:
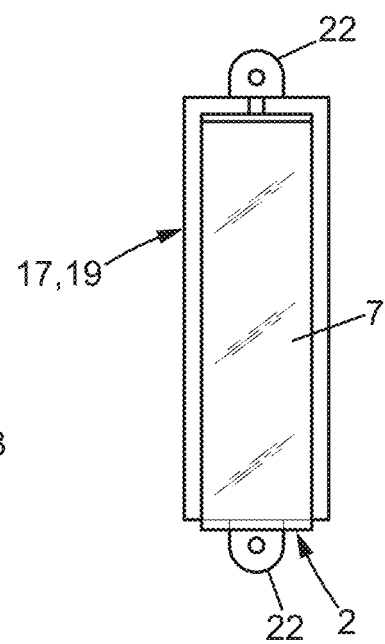
FIG. 6 is a view of the chemical sensor on a carrier.
Figure 7:
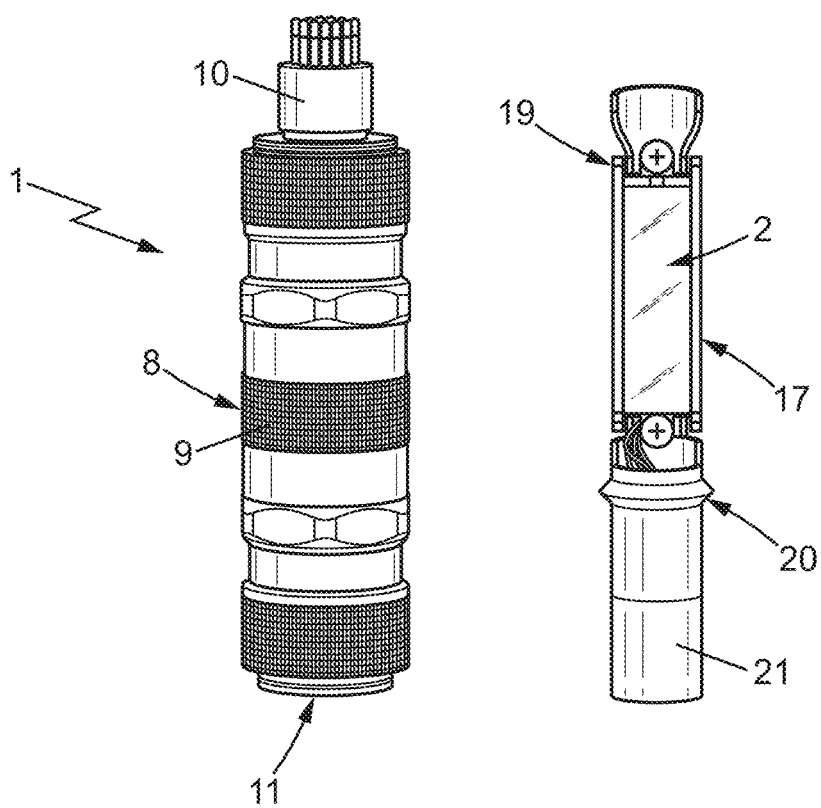
FIG. 7 is an exploded view of the detection device in two parts, a control unit and a chemical head.

According to the example illustrated in the figures, the chemical sensor 2 is present in the form of a thin plate, comprising a substrate 4 such as a glass plate. The glass plate 4 has two opposite sides, at least one of which is functionalised as explained hereinbelow. Alternatively, as shown in FIGS. 1 and 2, the two opposite sides of the glass plate 4 can be functionalised. More specifically, a layer, called a functionalised carrier 5, is bonded onto at least one side of the substrate 4. The functionalised carrier 5 is defined as having two functions. A first function is to bind itself to one side of the substrate 4. The second function is to detect the species to be analysed and accumulate same. For example, in order to detect a mercury compound in liquid form, the functionalised carrier 5 can comprise thiol-type functional groups secured to the glass carrier via organosilane bonds. In order to capture mercury in gaseous form and most other dissolved chemical forms of Hg, the functionalised carrier 5 can instead be a layer of gold, bound to the substrate via coating, and capturing the mercury by amalgamation.

In a more general manner, the nature of the substrate 4 and of the functionalised carrier 5 is chosen according to the one or more chemical species to be captured.

A diffusive layer 6 can be superimposed onto each functionalised carrier 5, said layer being intended to promote adsorption of the chemical substance in question and guide it towards the functionalised carrier 5 under the diffusion phenomenon. For example, in the event that it is intended to trap mercury, the diffusive layer 6 can comprise an Agarose gel. The diffusive layer 6 comprises pores, the size of which can vary depending on the analysis to be performed. For example, again using the example of mercury, when intending to trap labile species of MeHg and inorganic mercury, the pores preferably measure 20 nm (nanometres) at most. When intending to also trap more complex species, the size of the pores is increased, for example up to 450 nm. The diffusive layer 6 therefore performs two functions: it ensures the diffusion of the species therein, and selects a maximum species size capable of being diffused. Each diffusive layer 6 therefore has a free upper surface 7, capable of being in contact with the medium to be analysed. As explained hereinbelow, the diffusive layer 6 is optional. The description hereinbelow considers the example of a sensor 2 with a diffusive layer 6.

The chemical sensor 2 therefore has a parallelepipedal shape as a whole, two opposite sides of which are formed by the free surfaces 7 of the diffusive layers 6. The dimensions of the chemical sensor 2 are, according to one example embodiment, 76 mm (millimetres) by 26 mm, for a thickness, formed by superimposing layers 5, 6 on the substrate 4, of about 1 mm. The available surface area of the chemical sensor 2 that can come into contact with the medium to be analysed can comprise one or both of the free sides 7.

The vibration generating system 3 comprises, for example, a micro-motor µMOT, which is connected to the chemical sensor 2 and to control means CONT of the micro-motor µMOT. The control means CONT in particular comprise a microcontroller and a voltage generator used to control the frequency and intensity of the vibrations of the micro-motor µMOT by modifying the power supply voltage thereof. The vibration generating system 3 can further comprise other instruments used to monitor the operation of the device 1. For example, the vibration system 3 comprises a vibration sensor CAP, which is connected to the chemical sensor 2, in order to record the frequency at which the chemical sensor 2 effectively vibrates. The sensor CAP is typically an accelerometer. The information originating from the vibration sensor CAP is processed by the control means CONT and recorded in a memory MEM. The vibration frequency is preferably corrected in real time using the control means CONT, which analyse the vibration frequency provided by the accelerometer and regulate the power supply voltage of the micro-motor µMOT as a function thereof.

The generating system 3 further comprises actuation means for activating, stopping or programming vibrations. According to a first example, the vibration generating system 3 can be activated or stopped manually, for example by pressing a switch that can be accessed from outside the device 1. According to a second example, the vibration generating system 3 can be activated or stopped remotely. In such a case, the control means CONT comprise means for receiving an actuation signal. An external device can be used to generate and transmit the actuation signal to the receiving means. Such a device can, for example, be a Smartphonetype device. Vibrations can also be programmed to start at one or more moments in time and for one or more given durations.

The vibration frequency lies in the range 2 Hz to 1000 Hz, and preferably in the range 20 to 600 Hz.

The detection device 1 can be present, for example, in the general shape of a tube, allowing for the easy handling thereof. More specifically, according to one embodiment, the detection device 1 can be broken down into two parts.

A first part, called the control unit 8, integrates, for example, the control means CONT and the memory MEM of the vibration generating system 3. The control unit 8 comprises an impermeable cylindrical casing 9 made, for example, from plastic material, in which the components CONT and MEM are housed. A power supply, for example a battery, can also be placed in the unit 8. The control unit 8 is provided with an impermeable connection tip 10 at the first end thereof. The control unit 8, at the second end thereof, comprises a housing 11 for a set 12 of additional sensors, allowing for the provision of additional data on the environment in order to improve knowledge of the environment and thus the subsequent processing of the measurements by the device 1. For example, the set 12 of additional sensors can comprise a light sensor 13 and a temperature and pressure sensor 14 for detecting the properties of the medium in which the device 1 is immersed. A set 15 of light indicators can potentially be placed in the housing 11 in order to provide a visual indication of the status of the device 1 (in operation, stopped, low battery, etc.). The set 12 of additional sensors placed in the housing 11 of the control unit 8 is covered with a transparent, impermeable resin for the protection thereof while allowing the measurements to be made. The unit 8 can also house means for determining the position and positional changes of the device 1. For example, said means can be a GPS module in order to determine the geographic location of the device 1 and any possible movements thereof. Said means can also be an accelerometer and gyroscope set, used to determine the orientation of the device 1, for example to determine whether the device 1 is correctly in the horizontal or vertical position during the period of immersion thereof in the medium to be analysed. Knowledge of the orientation of the device 1 allows the actuation of the vibrations of the device 1 to be corrected, where necessary. Means can also be provided to determine the depth at which the device is immersed. The measurements taken by the set 12 of additional sensors, and those regarding the position or positional changes thereof are thus recorded in the memory MEM of the vibration generating system 3. A closure 16 can be placed on the control unit 8 to cover the housing 11 and the set 12 of additional sensors, in particular in order to protect the device during transport. This closure 16 is removed when the device is immersed into the medium to be analysed.

The second part is called the chemical head 17 and comprises the chemical sensor 2, the micro-motor μMOT and the vibration sensor CAP. More specifically, the chemical head 17 comprises a first support 18, in the form of a rectangular plate, for example made from plastic. The first support 18 comprises housings for the micro-motor μMOT and for the vibration sensor CAP. A silicone gel is deposited on top of the assembly, such that the micro-motor μMOT and the vibration sensor CAP are held in place on the first support 18. The chemical head 17 comprises a second support 19 for the chemical sensor 2. The second support 19 is also present in the form of a rectangular plate, the dimensions of which are substantially equal to those of the first support 17, and which can be made from plastic, and which forms a housing for the chemical sensor 2. Means for clipping, bonding or holding by magnetisation can be provided to secure the chemical sensor 2 and the second support 19 thereof to the support 18. According to the embodiment shown in FIG. 3 and FIGS. 6 to 9, the chemical sensor 2 has a single free upper surface 7 of the diffusive layer 6 intended to detect the chemical species. Finally, the chemical head 17 comprises a common support 20, allowing the first support 18 provided with the micro-motor μMOT and the vibration sensor CAP, in addition to the second support 19 provided with the chemical sensor 2, to be assembled thereto. The common support 20, also made from plastic, further comprises an impermeable connection tip 21, complementing the connection tip 10 of the control unit 8. For example, the connection tip 10 of the control unit 8 comprises pins that complement the receivers on the connection tip 21 of the chemical head 17.

The chemical head 17 is assembled as follows.

The micro-motor μMOT and the vibration sensor CAP are both electronically connected, via wires, to the connection tip 21 of the chemical head 17.

The chemical sensor 2 is positioned on the second support 19, which is then secured to the first support 18. For this purpose, the first support 18 and the second support 19 are both provided with perforated tabs 22 designed to secure the assembly thereof by means of screws or a magnetic holding system. The contact between the first support 18 and the second support 19 is made over the greatest surface area possible.

The two supports 18, 19 are then secured to the common support 20 using elastics, not shown in the figures. For this purpose, the first support 18 for example comprises hooks positioned near to the four corners thereof, onto each of which an elastic can be fixed. Similarly, the common support 20 comprises hooks for the elastics. The stiffness of the elastics is controlled such that the elastics act as dampers, limiting the transmission of the vibrations from the micro-motor μMOT to the common support 20 and thus to the rest of the device 1.

Therefore, almost all of the vibrations generated by the micro-motor μMOT are transmitted to the chemical sensor 2, via the wide contact surface between the supports 18, 19.

The chemical head 17 thus constituted can therefore be connected to the control unit 8 by plugging in the respective connection tip 10, 21 thereof. The connection tips 10, 21 provide an impermeable connection.

Finally, a removable cap, not shown, can cover the chemical head 17 for the protection thereof during transport and storage steps. The cap is removed when the device 1 is immersed into the medium to be analysed.

The parts made from plastic, in particular the casing 9 of the unit 8, the closure 16 and the cap, and the supports 18, 19 and 20 can be made, for example, by casting or 3D printing.

The embodiment thus described comprises a single chemical sensor 2 having a single free upper side 7. However, the device can comprise a plurality of chemical sensors 2 made to vibrate by the same micro-motor. For example, the device can comprise two chemical sensors 2, each having a single side in contact with the medium to be analysed, and each of which is secured to a support similar to the second support 19 disclosed, however positioned on either side of the first support 18, such that the same micro-motor μMOT can make the two chemical sensors 2 vibrate.

Therefore, the detection device 1 is easily transported to the in-situ place of deployment, for example on the bank of a river, at sea to at any other body of water. The device 1 can be programmed in advance by connecting it to an IT system, in particular via the connection tip 10 of the unit 8 before assembling the chemical head 17. This connection can also be used to charge the batteries of the device in the unit 8. When the device 1 must be used, the cap and the closure 16 are removed, and the device 1 is immersed in water. The vibration generating system 3 is then activated in order to transmit the vibrations to the chemical sensor 2. The actuation means can be used to vary the vibrations applied to the chemical sensor 2 over time. The species to be analysed diffuse from the medium to be analysed to the functionalised carrier 5, on or in which they accumulate. The accumulation time on the functionalised carrier 5 is controlled by the vibration dynamic. Indeed, in the absence of vibrations, almost no diffusion can be considered to have taken place. Therefore, by programming the period of time during which the vibration generating system 3 is activated, the diffusion time is also controlled. In other words, the command to activate and stop the vibration generator 3 can constitute a switch controlling the diffusion phenomenon within the one or more chemical sensors 2.

The device 1 is then retrieved; the cap and closure 16 are repositioned, and the device 1 can be transported, for example to a laboratory for analysing the trapped species. The chemical head 17 can be disconnected from the unit 8 in order to ease the processing of the chemical sensor 2. The data recorded in the memory MEM in the unit 8, such as the data from the set 12 of additional sensors and the log of the vibrations applied to the chemical sensor 2 and of the positions thereof, is thus easy to retrieve. For example, the connection tip 10 of the unit 8 is used to connect the device to an IT system. The chemical sensor 2 is disassembled from the chemical head 17 in order to be analysed. For example, an elution method can be implemented on the chemical sensor 2 in order to retrieve the species captured and analyse same. The functionalised carrier 5 is replaced for each in-situ sampling operation by changing the chemical sensor 2.

Once the species captured are retrieved, the concentration of said species in the medium to be analysed is deduced with improved accuracy relative to the devices of the prior art. Indeed, as explained hereinabove, the calculation of the concentration is based on Fick equations. In a conventional manner, experiments are conducted in a laboratory in order to produce models for applying the Fick equations. With the DGT-type sensors of the prior art, the models developed in a laboratory do not represent the reality in the field as the agitation conditions in the medium to be analysed can only be approximated by the laboratory models. For example, the diffusion coefficient determined in a laboratory cannot correspond to that in the field, due to the presence of the DBL, the thickness of which is unknown. Thanks to the detection device 1 comprising the vibration generating system 3, the vibrations applied to the chemical sensor 2 during the measurements taken in the medium to be analysed are identical to those applied in a laboratory. In particular, the vibration sensor CAP measures the vibrations to which the chemical sensor 2 is actually subjected, and thus is used for control based on feedback, taking into account the agitation of the medium in which the device 1 is immersed, such that the vibrations actually applied to the chemical sensor 2 are known and the model to be applied can be chosen accordingly.

Moreover, by making the chemical sensor 2 vibrate using the micro-motor μMOT, the thickness of the DBL ("Diffusive Boundary Layer") presented in the introduction hereto is controlled. Indeed, the agitation created by the vibrations around the chemical sensor 2 acts on the renewal of the species near to the upper sides 7 of the diffusive layers 6. Therefore, the stronger the vibrations, the faster renewal occurs and the lower the thickness of the DBL. There are numerous advantages to this control. It in particular reduces the diffusion time, i.e. the time required for the species to pass from the medium to be analysed to the functionalised carrier 5.

By controlling the thickness of the DBL, the influence thereof on the diffusion phenomenon is known, such that the implementation of a minimum thickness of the diffusive layer 6 is not required. More specifically, a diffusion pathway can be defined as being the thickness passed through by the species to be analysed and within which the diffusion phenomenon takes place between the medium to be analysed and the functionalised carrier 5. Therefore, in other words, the diffusion pathway is defined as being the sum of the thickness of the DBL and the thickness of the diffusive layer 6. Given that the thickness of the diffusive layer 6 can be significantly reduced, the diffusion pathway, and thus the diffusion time can be significantly reduced.

In extreme cases, the diffusive layer 6 can be removed entirely, such that the DBL alone suffices as the foundation of the diffusion phenomenon. However, as previously stated, the implementation by the diffusive layer 6 of a selection based on the size of the species to be captured can be advantageous. According to one embodiment, the thickness of the resin layer 6 is less than one micrometre, or is less than 100 nanometres.

Figure 10:
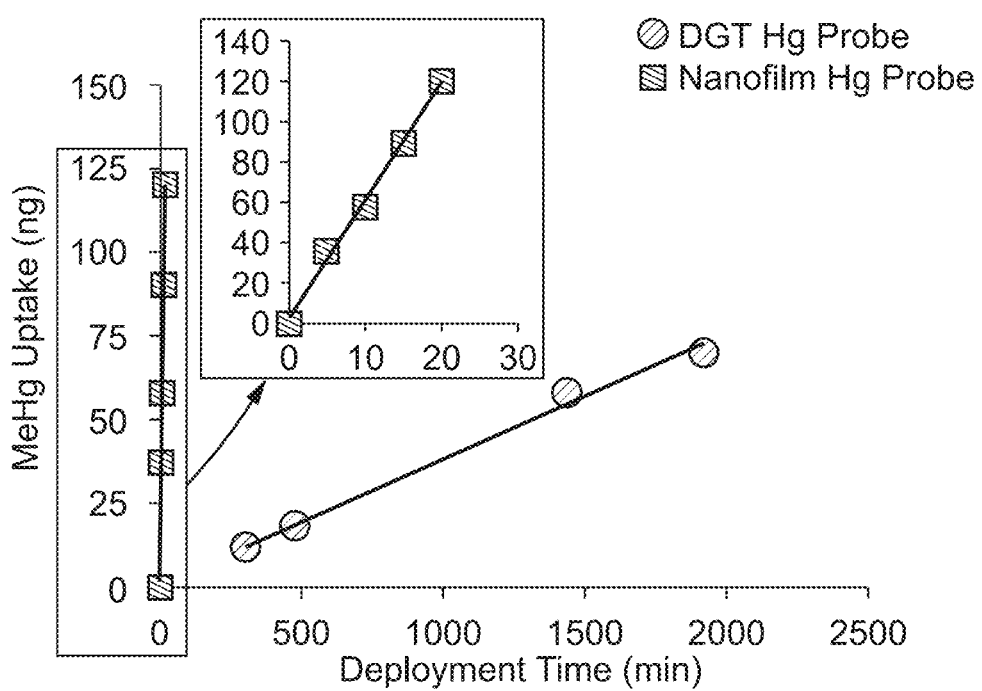
FIG. 10 is a graph comparing the performance levels of the device in the previous figures with a DGT-type device of the prior art.
Figure 8:
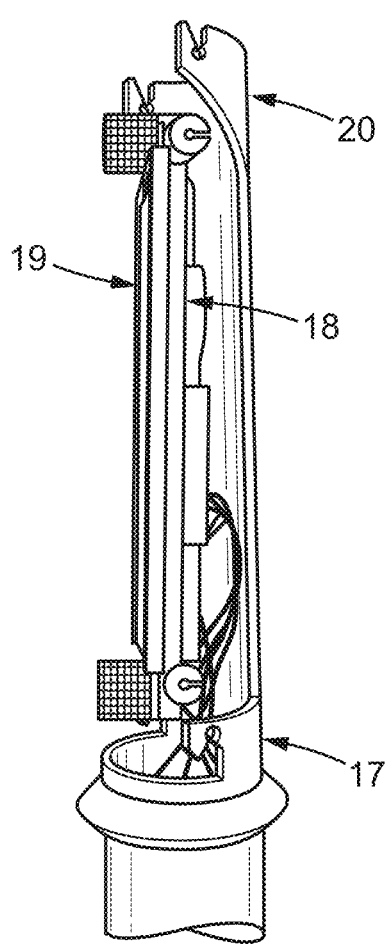
FIG. 8 is a side view of the chemical head in FIG. 7.
Figure 9:
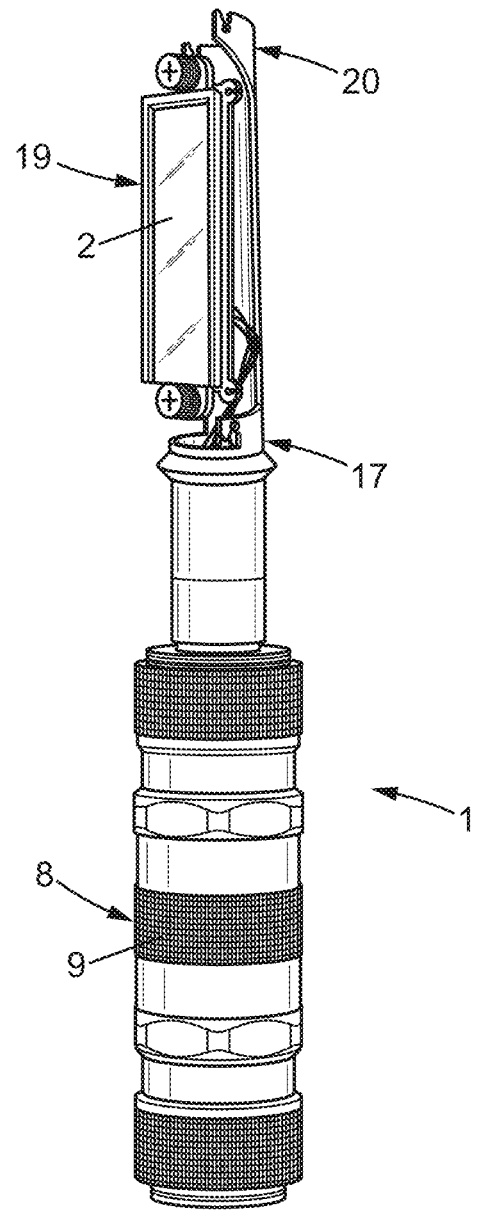
FIG. 9 is a view of the assembled detection device.

In order to compare the diffusion rates of the DGT sensor of the prior art with the detection device 1, a measurement was taken measuring in time the quantity of MeHg captured by a DGT-type chemical sensor of the prior art ("Hg DGT sensor"), without any vibration generating system, and that captured by the device 1 according to the invention ("Hg Nanofilm Sensor"), with a vibration generator 3, in the absence of any diffusive layer 6. FIG. 10 shows the results for the two devices, the quantity of MeHg being measured in nanograms and the time in minutes.

For the DGT device, the straight line representing the quantity of MeHg captured in time has a slope that is significantly less than 1, equal to about 0.03. The diffusion time is measured in hours or in days.

Conversely, for the device according to the invention, the straight line representing the quantity of MeHg captured in time has a slope that exceeds 1, equal to about 5, whereby the diffusion time is measured in minutes.

Therefore, the diffusion rate of the DGT device of the prior art is much lower than that of the device 1 according to the invention. For the same quantity of captured MeHg, the diffusion within the device according to the invention has been measured to occur 160 times faster than that within a device according to the prior art. The addition of the vibration generating system 3 to the device 1 according to the invention thus allows a quantity of MeHg capable of being used to perform concentration measurements to be very quickly obtained.

The paragraphs below will now disclose one example of a method for manufacturing the chemical sensor 2 designed to obtain low thicknesses for the layers 5, 6.

In a first step, at least one side of a plate is etched; in practice two opposite sides are etched, to form the substrate 4. Thus, when the substrate is made from glass, the etching releases oxygen-hydrogen bonds (OH bonds). The functionalised carrier 5 is then applied as a layer onto the etched side. Given that the substrate is made from glass, the functionalised carrier 5 adheres to the substrate to form, for example, an organosilane bond with the glass and forms a layer about 0.7 nm thick. Finally and optionally, the diffusive layer 6 is deposited on the functionalised carrier 5 by a spin-coating or dip-coating method, allowing the aforementioned thicknesses to be achieved. The presence of the diffusive layer 6 is optional. The size of the pores in the diffusive layer 6 can be adapted, for example by modifying the Agarose concentration, in order to select the size of the species that are diffused.

The design of the chemical sensor 2 potentially allows both sides of the substrate to be used, so as to obtain two free upper surfaces 7 for detecting the species to be analysed. The diffusion surface area is thus doubled in relation to the case wherein diffusion takes place via a single surface. The quantity of species captured by the device 1 is also doubled.

The device 1 thus formed has many advantages.

For example, the device 1 does not need to be monitored over a long period of time, which reduces costs. The quantity of species captured is sufficient after only a few minutes.

Moreover, the device 1 is present in the form of a tube, which is easy to handle as it simple requires being immersed into the medium to be analysed, then retrieved by hand or secured to a cord. Therefore, the device 1 is suitable for all users and is not reserved to informed operators.

Finally, the chemical head 17, on which is integrated the chemical sensor 2, can be separated from the electronic part of the device contained in the control unit 8. Therefore, when a chemical sensor 2 has been used, it can be easily replaced by a new chemical sensor 2. The chemical sensor 2 can therefore be chosen to suit the desired analysis and the species to be captured. Given that the control unit 8 can be reused, the same control unit 8 can be used for different chemical heads 17, comprising different chemical sensors 2, i.e. intended to capture different chemical species. For example, one application has been mentioned for detecting mercury species. However, the device can be adapted to suit other applications, for example to detect other pollutants, in addition to the detection of biological species. For example, the chemical sensor 2 can be a DNA chip.

Thanks to reusable and adaptable parts, the usage costs of the device 1 are reduced.

The manufacture of certain parts such as the unit 8 and the supports 18, 19, 20 from plastic also reduces the production costs of the device 1.

Alternatives to the device 1 can be considered. In particular, the device 1 was previously described as comprising two parts, the unit 8 and the chemical head 17, said parts being able to connect to each other in a removable manner via the impermeable connection tip 10.

However, in one alternative embodiment not illustrated, the tip 8 and the chemical head 17 are rigidly connected to each other. Moreover, they cannot be disconnected from each other. In other words, the device 1 is present in the form of a single unit. Said unit is impermeable, with the exception that it has an area intended for placing the set 12 of sensors in communication with the external environment.

Within the scope of this alternative embodiment, the device 1 is devoid of any impermeable connection tip. The elements of the unit 8 and of the chemical head 17 disclosed hereinabove are arranged within a single casing, onto which the aforementioned cap and closure can be placed.

Further to these elements, the device 1 comprises a wireless communications device, forming a communications interface for the data exchanges taking place between the device 1 and the outside. The communications device is connected to all or part of the elements of the device 1, and thus authorises the transmission and receipt of data for the operation of said elements in addition to the collection of data.

Within the scope of this alternative embodiment, the power source contained inside the device 1, for example a battery, can advantageously be recharged with electrical power remotely, for example by induction.

It should be noted that, as a result of the configuration of the device according to this alternative embodiment, the relative arrangement of the elements contained therein can be easily adjusted. For example, in one embodiment of this alternative embodiment, the power source is located at one end of the device, whereas the set 12 of additional sensors and the communications device are located at another end of the device.

This alternative embodiment of the device prevents the need for the presence of an impermeable connection tip, which is an expensive element that tends to substantially increase the cost of the device 1.

The invention claimed is:

1. A detection device for detecting at least one chemical species in a medium to be analyzed comprising:
    a chemical sensor comprising:
        a substrate, and
        at least one functionalized carrier configured to capture and accumulate the chemical species and attached to a side of the substrate, and
        a diffusive layer superimposed on the at least one functionalized carrier; and
    a vibration generating system connected to the chemical sensor and configured to generate a diffusion phenomenon between the medium to be analyzed and the at least one functionalized carrier by subjecting the chemical sensor to controlled vibrations, the vibration generating system comprising a vibrating micro-motor connected to the chemical sensor and to a controller of the micro-motor, the controller comprising a microcontroller and a voltage generator used to control a frequency and an intensity of the controlled vibrations.

2. The detection device according to claim 1, wherein the thickness of the diffusive layer is less than 1 micrometer.

3. The detection device according to claim 2, wherein the thickness of the diffusive layer lies in the range 250 nm to 10 nm.

4. The detection device according to claim 1, wherein the diffusive layer is made from Agarose gel.

5. The detection device according to claim 1, wherein the thickness of the at least one functionalized carrier is less than 1 micrometer.

6. The detection device according to claim 5, wherein the thickness of the at least one functionalized carrier is less than 1 nm.

7. The detection device according to claim 1, wherein the at least one functionalized carrier comprises two functionalized carriers, and
    the substrate comprises two opposite sides, on each of which is adhered one of the two functionalized carriers.

8. The detection device according to claim 1, wherein the vibration generating system comprises a vibration sensor connected to the chemical sensor.

9. The detection device according to claim 1, wherein the vibrating micro-motor is a high-frequency vibrating micro-motor.

10. The detection device according to claim 1, further comprising both a control unit in which the controller of the micro-motor is disposed, and a chemical head comprising the chemical sensor and the vibration generating system, the control unit and the chemical head being configured to remove from each other and each comprising at least one connection tip for the assembly thereof with each other.

11. The detection device according to claim 1, wherein the detection device is a single unit.

\* \* \* \* \*